Feb. 7, 1967 A. B. LAMBERT Plant Pat. 2,711
PIERIS
Filed Feb. 8, 1966
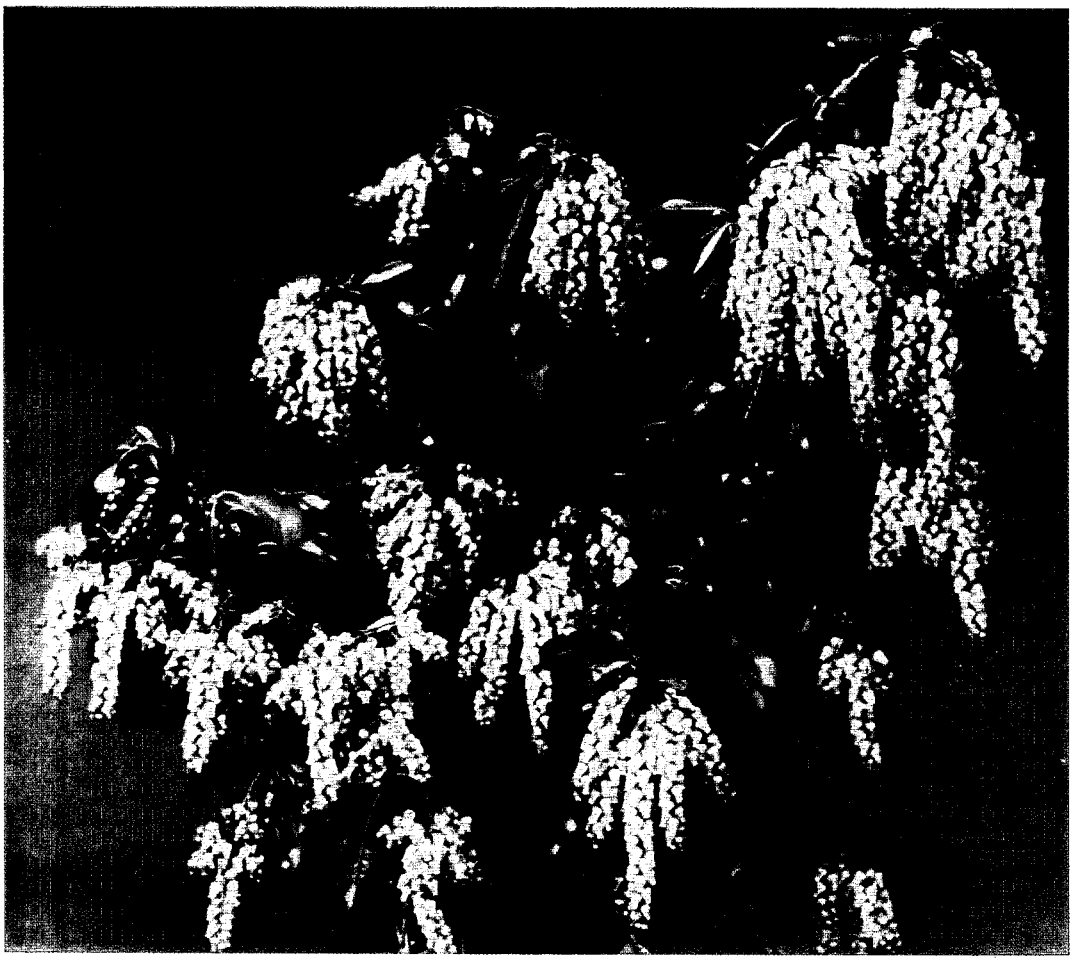
INVENTOR
ANDREW B. LAMBERT
By Eugene M. Eckelman
ATTORNEY United States Patent Office Plant Pat. 2,711
Patented Feb. 7, 1967

2,711
PIERIS
Andrew B. Lambert, 5120 SE. 28th Ave.,
Portland, Oreg. 97202
Filed Feb. 8, 1966, Ser. No. 526,002
1 Claim. (Cl. Plt.—54)

This invention comprises a new and distinct variety of *Pieris japonica,* commonly known as Andromeda. The *Pieris japonica* of the invention is the result of a sport which was taken from a parent plant and which has distinct color characteristics.

The sport was discovered by me in the spring of 1960 in my nursery located at 5120 SE. 28th Avenue, Portland, Oregon, at which time it was apparent that the pink coloration of the flowers of the sport persisted in such original coloration even when the flowers were fully open, whereas it is a known characteristic of the flower of *Pieris japonica* that the flower originally buds in pink but the pink coloration thereof rapidly fades into a very light pink or white color as the bud opens. Cuttings were made by me in Portland, Oregon from the parent plant and observed for five years. Each plant developed from the cultivated sport maintained the same characteristics of producing a pink bloom persisting in its initial pink coloration even when fully open.

The accompanying illustration shows one of the plants in bloom.

The following is a detailed description of the plant and its flowers:

*Form.*—The form of the plant appears to be identical with the commonly known and commercialized *Pieris japonica.*

*Foliage.*—The foliage also appears to be identical with the commonly known and commercialized *Pieris japonica.*

*Flowers.*—The flowers also assume the pink coloration of the commonly known and commercialized *Pieris japonica,* are of the same general size, and also are of the same structure. The characteristics of the flower differ, however, in that as stated the pink coloration thereof persists even when the flower is fully open.

*Characteristics of growth and blooming.*—The plant is grown under the usual growing conditions of the commonly known and commercialized *Pieris japonica.* The time of flowering is also the same, namely in the spring under ordinary conditions. The plant is well suited for forcing, with the flower under such forcing maintaining its lasting color characteristics.

Having thus disclosed my invention, I claim:

The new and distinct variety of *Pieris japonica* plant substantially as herein disclosed, characterized particularly by its flower wherein said flower maintains its pink coloration when in the budding stage and when fully open.

No references cited.

ABRAHAM G. STONE, *Primary Examiner.*
ROBERT E. BAGWILL, *Examiner.*